United States Patent
Tsuruta et al.

(10) Patent No.: US 10,330,916 B2
(45) Date of Patent: Jun. 25, 2019

(54) OPTICAL-FIBER SCANNER, ILLUMINATION APPARATUS, AND OBSERVATION APPARATUS

(71) Applicant: OLYMPUS CORPORATION, Tokyo (JP)

(72) Inventors: Hiroshi Tsuruta, Kanagawa (JP); Yasuaki Kasai, Saitama (JP); Hirokazu Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 116 days.

(21) Appl. No.: 15/588,789

(22) Filed: May 8, 2017

(65) Prior Publication Data

US 2017/0242239 A1 Aug. 24, 2017

Related U.S. Application Data

(63) Continuation of application No. PCT/JP2014/079979, filed on Nov. 12, 2014.

(51) Int. Cl.
*A61B 1/00* (2006.01)
*A61B 1/07* (2006.01)
(Continued)

(52) U.S. Cl.
CPC ...... *G02B 23/2469* (2013.01); *A61B 1/00172* (2013.01); *A61B 1/07* (2013.01); *G02B 26/103* (2013.01)

(58) Field of Classification Search
CPC .............. G02B 23/2469; G02B 26/103; A61B 1/00172; A61B 1/07
See application file for complete search history.

(56) References Cited

U.S. PATENT DOCUMENTS 7,129,472 B1 * 10/2006 Okawa ............... A61B 1/00059
  250/234
7,496,259 B2 * 2/2009 Karasawa .......... A61B 1/00096
  385/118
(Continued)

FOREIGN PATENT DOCUMENTS

EP      2730212 A1   5/2014
JP   2010-523198 A   7/2010
(Continued)

OTHER PUBLICATIONS

International Search Report dated Dec. 16, 2014 issued in PCT/JP2014/079979.

*Primary Examiner* — William N Harris
(74) *Attorney, Agent, or Firm* — Scully, Scott, Murphy & Presser, P.C.

(57) ABSTRACT

Provided is an optical-fiber scanner including: an optical fiber; a body fitted on a basal-end side of the optical fiber; piezoelectric elements secured to the body and causing the optical fiber to vibrate; and a securing portion to which the body is fitted at a position that is farther on a basal-end side away from the piezoelectric elements, wherein the body has a columnar portion that is formed of an elastic material to which the piezoelectric elements are attached and that has a through-hole into which the optical fiber can be inserted, and a distal-end portion that is disposed at a distal end of the columnar portion, that supports the optical fiber in a fitted state, and that has a rotator shape in which a cross-sectional area thereof in a radial direction gradually decreases toward a distal end of the optical fiber.

5 Claims, 9 Drawing Sheets (51) Int. Cl.
*G02B 23/24* (2006.01)
*G02B 26/10* (2006.01)

(56) References Cited

U.S. PATENT DOCUMENTS

| | | | |
|---|---|---|---|
| 7,583,872 B2 * | 9/2009 | Seibel | A61B 1/0008 385/25 |
| 2008/0249369 A1 | 10/2008 | Seibel et al. | |
| 2009/0092364 A1 * | 4/2009 | Johnston | A61B 1/00096 385/117 |
| 2009/0103882 A1 * | 4/2009 | Melville | A61B 1/0008 385/137 |
| 2014/0114131 A1 | 4/2014 | Sakai et al. | |
| 2015/0029570 A1 * | 1/2015 | Ito | G02B 23/26 359/198.1 |

FOREIGN PATENT DOCUMENTS

| | | |
|---|---|---|
| JP | 2010-284261 A | 12/2010 |
| JP | 2011-217835 A | 11/2011 |
| JP | 5452781 B1 | 3/2014 |
| WO | WO 2008/123859 A1 | 10/2008 |
| WO | WO 2014/002556 A1 | 1/2014 |

* cited by examiner

OPTICAL-FIBER SCANNER, ILLUMINATION APPARATUS, AND OBSERVATION APPARATUS

CROSS-REFERENCE TO RELATED APPLICATIONS

This is a continuation of International Application PCT/JP2014/079979, with an international filing date of Nov. 12, 2014, which is hereby incorporated by reference herein in its entirety.

TECHNICAL FIELD

The present invention relates to an optical-fiber scanner, an illumination apparatus, and an observation apparatus.

BACKGROUND ART

In the related art, there are known optical-fiber scanners with which illumination light is scanned on an imaging subject by emitting the illumination light while scanning the distal end of an optical fiber in a spiraling manner by making a piezoelectric element vibrate (for example, see Patent Literatures 1 and 2). The optical-fiber scanner described in Patent Literature 1 has a structure in which an optical fiber is inserted into a substantially cylindrical piezoelectric-element unit, and a portion of the optical fiber that is farther on the basal-end side from the distal end thereof is supported on the distal end of the piezoelectric-element unit by using an adhesive. In addition, the optical-fiber scanner described in Patent Literature 2 has a structure in which a portion of the optical fiber that is farther on the basal-end side from the distal end thereof is supported in a fitted state by using a support member, such as an annular interposed component, an annular plug, adhesive beads, or the like.

CITATION LIST

Patent Literature

{PTL 1} Japanese Unexamined Patent Application, Publication No. 2011-217835
{PTL 2} Japanese Translation of PCT International Application, Publication No. 2010-523198

SUMMARY OF INVENTION

A first aspect of the present invention is an optical-fiber scanner including: an optical fiber that guides light to emit the light from a distal end thereof; a vibration-transmitting body that is fitted to a portion farther on a basal end side of the distal end of the optical fiber and that can transmit vibrations to the optical fiber; a plurality of piezoelectric elements that are secured to the vibration-transmitting body, that are polarized in radial directions of the optical fiber, and that cause the optical fiber to vibrate via the vibration-transmitting body when alternating voltages are applied thereto in the polarization directions; and a support portion that has a fitting hole to which the vibration-transmitting body is fitted at a position that is farther on a basal-end side away from the piezoelectric elements, and that can support the optical fiber in a cantilever-like manner via the vibration-transmitting body fitted to the fitting hole, wherein the vibration-transmitting body has a hollow columnar portion that is formed of an elastic material, to which the plurality of piezoelectric elements are attached at side surfaces thereof, and that has a through-hole through which the optical fiber can be inserted, and a distal-end portion that is disposed at a distal end of the columnar portion, that supports the optical fiber in a fitted state, and that has a rotator shape in which a cross-sectional area thereof in a radial direction gradually decreases toward a distal end of the optical fiber.

A second aspect of the present invention is an illumination apparatus including: any one of the above-described optical-fiber scanners; a light source that generates the light to be guided by the optical fiber; a focusing lens that focuses the light emitted from the optical fiber; and an outer tube that holds the focusing lens and the optical-fiber scanner.

A third aspect of the present invention is an observation apparatus including: the above-described illumination apparatus; and a light-detecting portion that detects return light returning from an imaging subject and generated by radiating the light onto the imaging subject with the illumination apparatus.

DESCRIPTION OF EMBODIMENT

An optical-fiber scanner, an illumination apparatus, and an observation apparatus according to an embodiment of the present invention will be described below with reference to the drawings.

Figure 1:
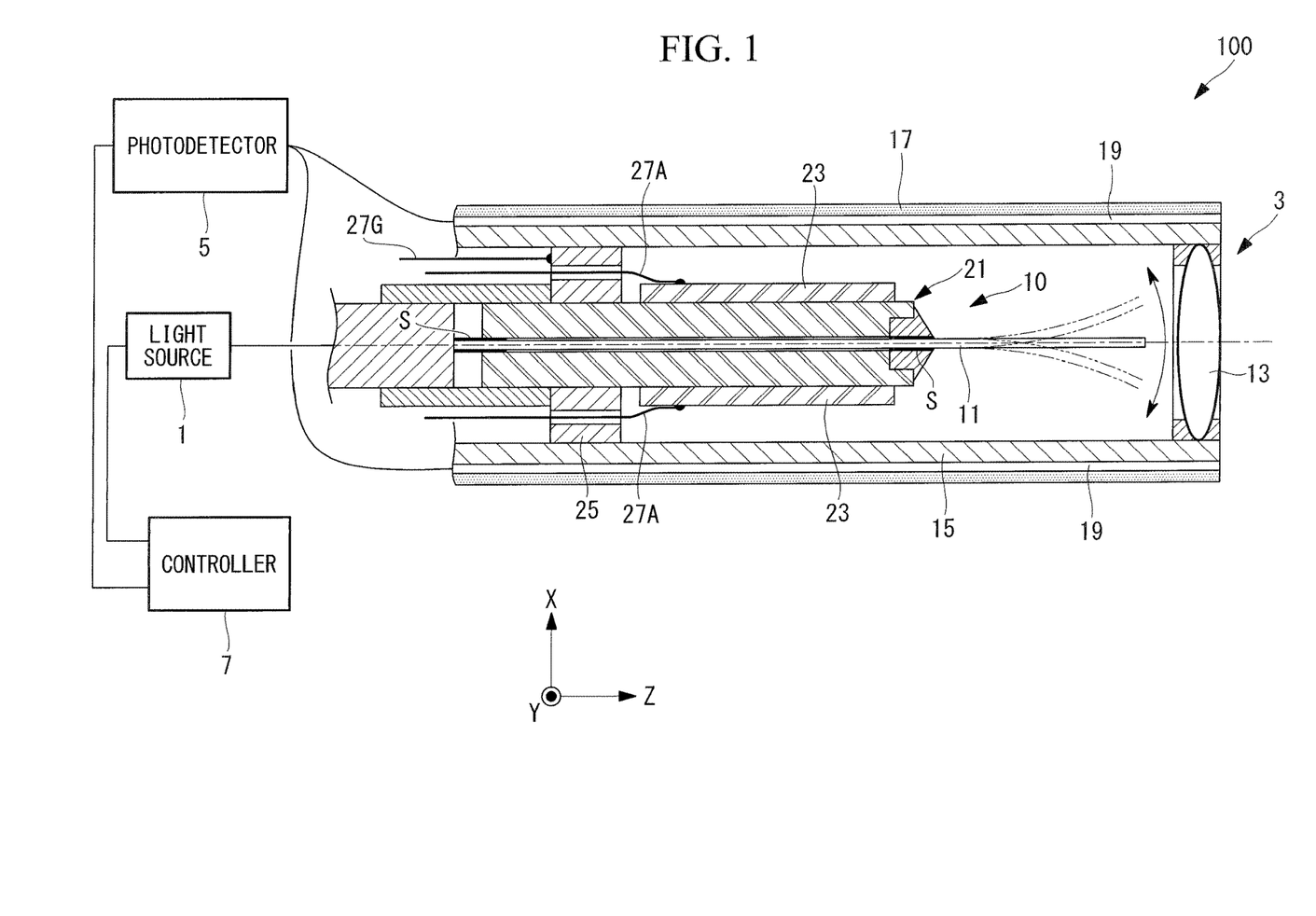
FIG. 1 is a cross-sectional view of an endoscope apparatus according to an embodiment of the present invention, taken along a radial direction of an illumination optical fiber.

As shown in FIG. 1, an endoscope apparatus (observation apparatus) 100 according to this embodiment is provided with: a light source 1 that generates illumination light; an illumination apparatus 3 that radiates the illumination light onto an imaging subject (not shown); a photodetector (light-detecting portion) 5, such as a photodiode, that detects return light, such as reflected light, fluorescence, or the like, returning from the imaging subject due to the irradiation with the illumination light; and a controller 7 that performs control or the like of the illumination apparatus 3 and the photodetector 5. In the following, the longitudinal direction of the endoscope apparatus 100 is assumed to be a Z-axis direction, and two directions that are orthogonal to the longitudinal direction of the endoscope apparatus 100 and that are orthogonal to each other are assumed to be an X-axis direction and a Y-axis direction, respectively.

The illumination apparatus 3 is provided with: an optical-fiber scanner 10 that has an illumination optical fiber 11 that guides the illumination light emitted from the light source 1 and that emits the illumination light from the distal end thereof; a focusing lens 13 that focuses the illumination light emitted from the illumination optical fiber 11; a long, thin cylindrical outer tube 15 that accommodates the optical-fiber scanner 10 and the focusing lens 13; a cover portion 17 that covers an outer circumferential surface of an outer tube 15; and a plurality of detection optical fibers 19 that are disposed between the outer tube 15 and the cover portion 17 and that guide the return light coming from the imaging subject to the photodetector 5.

The light source 1 and the photodetector 5 are disposed on the basal-end side of the optical-fiber scanner 10.

The controller 7 is provided with a CPU (not shown) that controls the illumination apparatus 3 and the photodetector 5 and a memory that stores a program for operating the CPU, various signals to be input to the CPU, and so forth.

Figure 2:
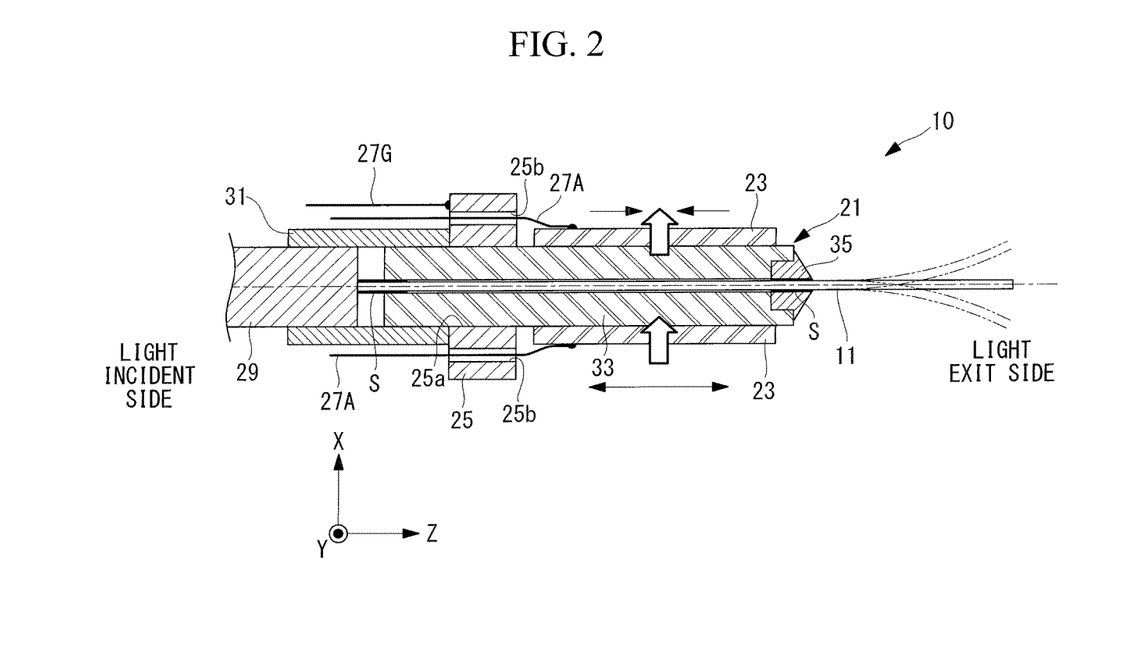
FIG. 2 is a cross-sectional view of an optical-fiber scanner in FIG. 1.
Figure 3:
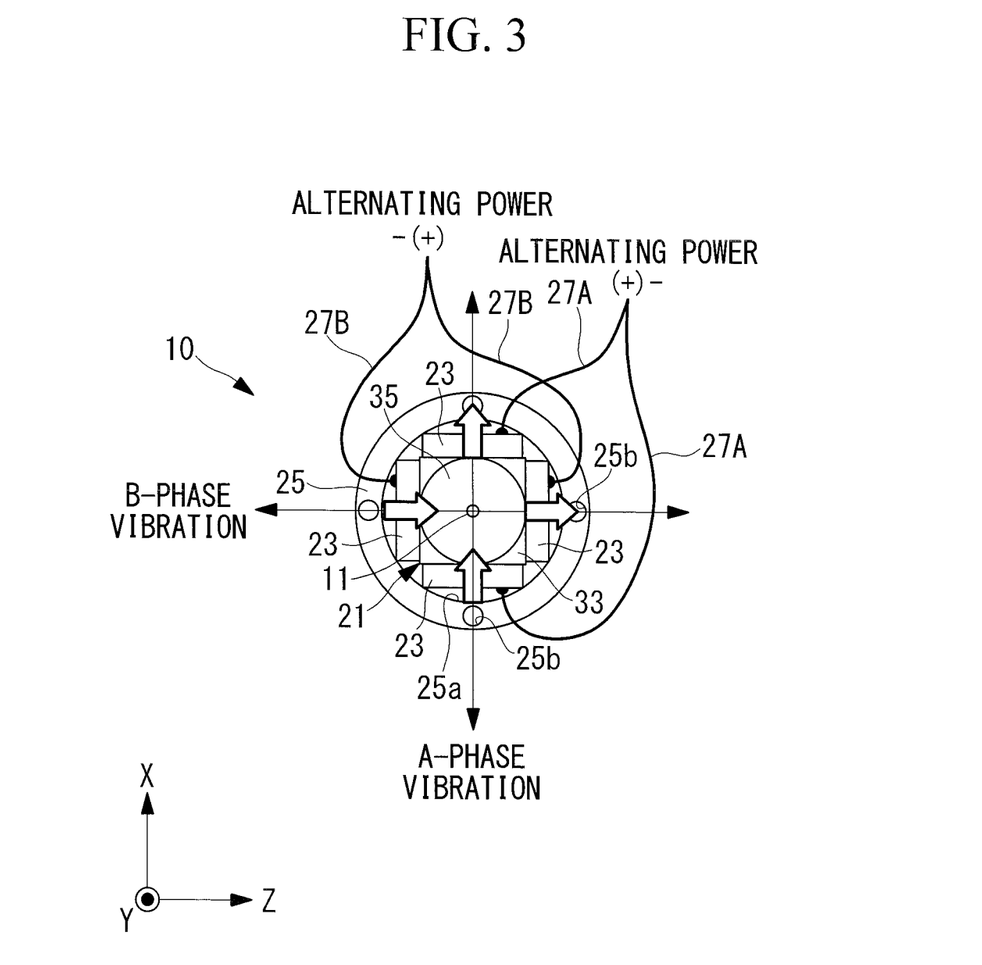
FIG. 3 is a cross-sectional view of a vibration-transmitting body and a securing portion in FIG. 2, taken along the radial direction of the illumination optical fiber.

As shown in FIGS. 2 and 3, the optical-fiber scanner 10 is provided with an illumination optical fiber (optical fiber) 11 such as a multi-mode fiber or a single-mode fiber; a vibration-transmitting body 21 that can transmit vibrations to the illumination optical fiber 11 by being fitted to a portion of the illumination optical fiber 11 farther on the basal-end side from the distal end thereof; four piezoelectric elements 23 secured to the vibration-transmitting body 21; a securing portion (support portion) 25 that supports the illumination optical fiber 11 via the vibration-transmitting body 21; a driving lead (GND) 27G; and four leads 27A and 27B.

In addition, the optical-fiber scanner 10 is provided with a jacket 29 that covers a portion of the illumination optical fiber 11 that is farther on the basal-end side than the vibration-transmitting body 21 is, and a buckling-prevention pipe 31 that protects the basal end of the illumination optical fiber 11.

The illumination optical fiber 11 is formed of a center material, referred to as a core, and a sheath material, referred to as a clad, that covers the outer side of the center material. The core and the clad have different refractive indexes from each other, and are respectively formed of quartz or a plastic material. In addition, as shown in FIG. 1, the illumination optical fiber 11 is disposed along the longitudinal direction of the outer tube 15, one end thereof extends to the exterior at the basal end of the outer tube 15 and is connected to the light source 1, and the other end thereof is disposed in the vicinity of the focal position of the focusing lens 13 inside the outer tube 15.

As shown in FIG. 2, the vibration-transmitting body 21 has a hollow columnar portion 33 that is formed of an elastic material and in which the piezoelectric elements 23 are attached to side surfaces thereof, and a distal-end portion 35 that is attached to the distal end of the columnar portion 33 and that supports the illumination optical fiber 11 in a fitted state. Both the columnar portion 33 and the distal-end portion 35 are formed of a nickel or copper material.

Figure 4A:
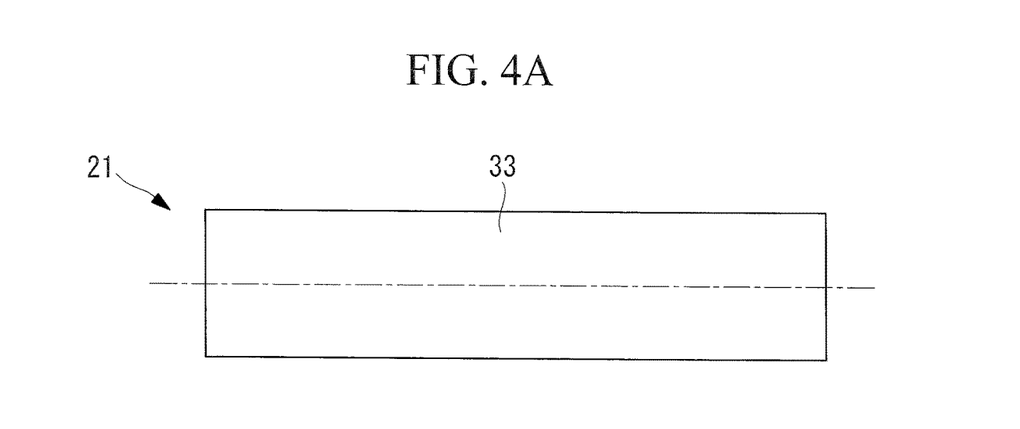
FIG. 4A is a side view of a columnar portion of the vibration-transmitting body in FIG. 2.
Figure 4B:
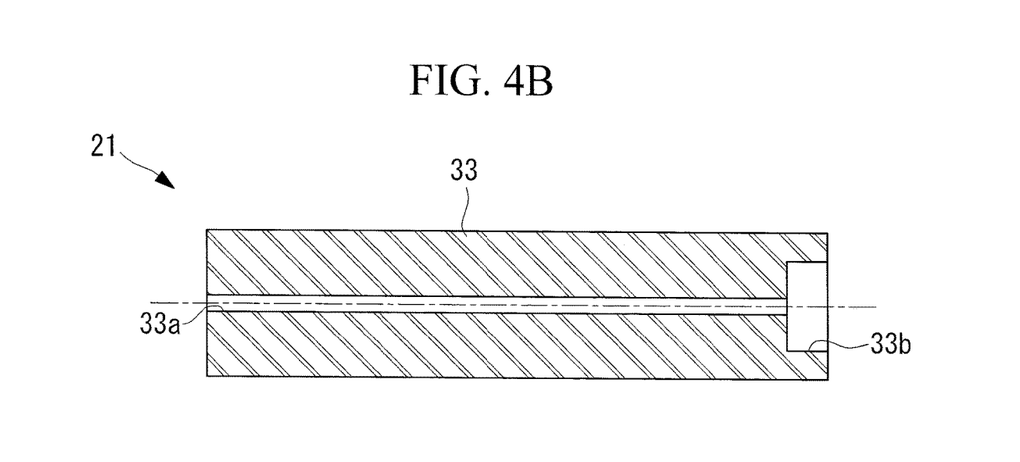
FIG. 4B is a cross-sectional view of the columnar portion of the vibration-transmitting body in FIG. 2, taken along the center axis.
Figure 4C:
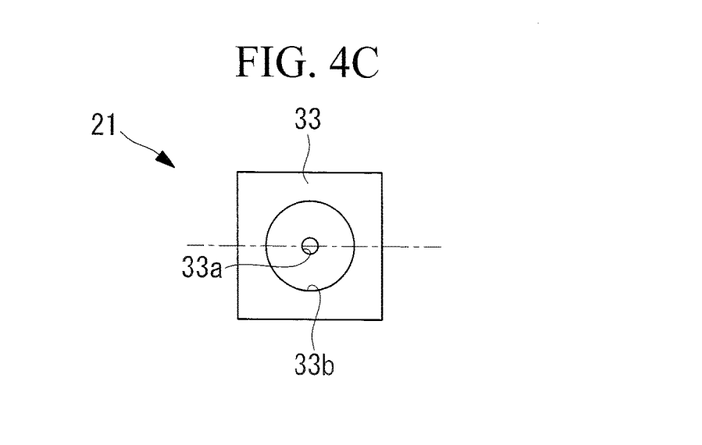
FIG. 4C is a plan view of the columnar portion of the vibration-transmitting body in FIG. 2, viewed in the direction along the center axis.

As shown in FIGS. 4A, 4B, and 4C, the columnar portion 33 has a through-hole 33a into which the illumination optical fiber 11 is inserted. As shown in FIG. 2, a basal-end portion of the through-hole 33a is configured so that the inserted illumination optical fiber 11 is attached thereto by means of an epoxy-based adhesive S applied to an outer circumferential surface of the illumination optical fiber 11.

In addition, the columnar portion 33 has, at one end thereof in the longitudinal direction, an opening 33b in which the shape thereof includes a level difference where the opening area of the through-hole 33a increases radially outward. This opening 33b is configured so that the distal-end portion 35 can be held in the fitted state. In addition, as shown in FIG. 3, the columnar portion 33 has a substantially square columnar external shape, and the piezoelectric elements 23 are attached to the respective four side surfaces by using the epoxy-based adhesive.

Figure 5A:
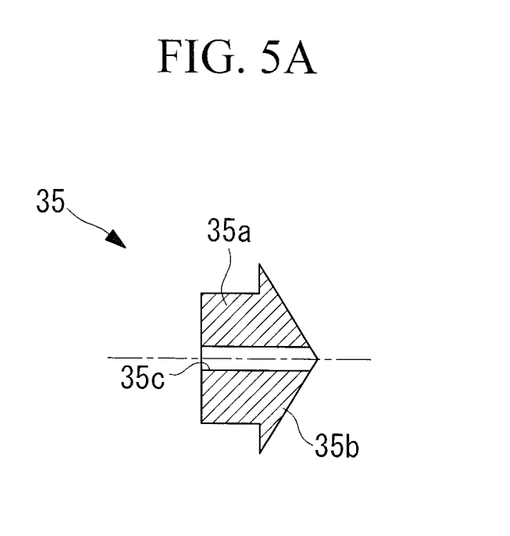
FIG. 5A is a cross-sectional view of a distal-end portion of the vibration-transmitting body in FIG. 2, taken along the center axis.
Figure 5B:
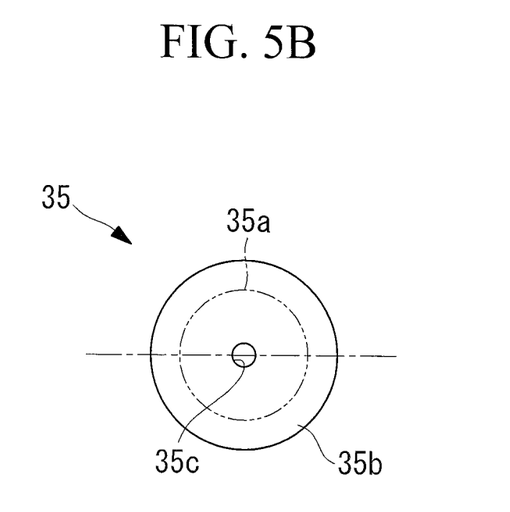
FIG. 5B is a plan view of the distal-end portion of the vibration-transmitting body in FIG. 2, viewed in the direction along the center axis.
Figure 6:
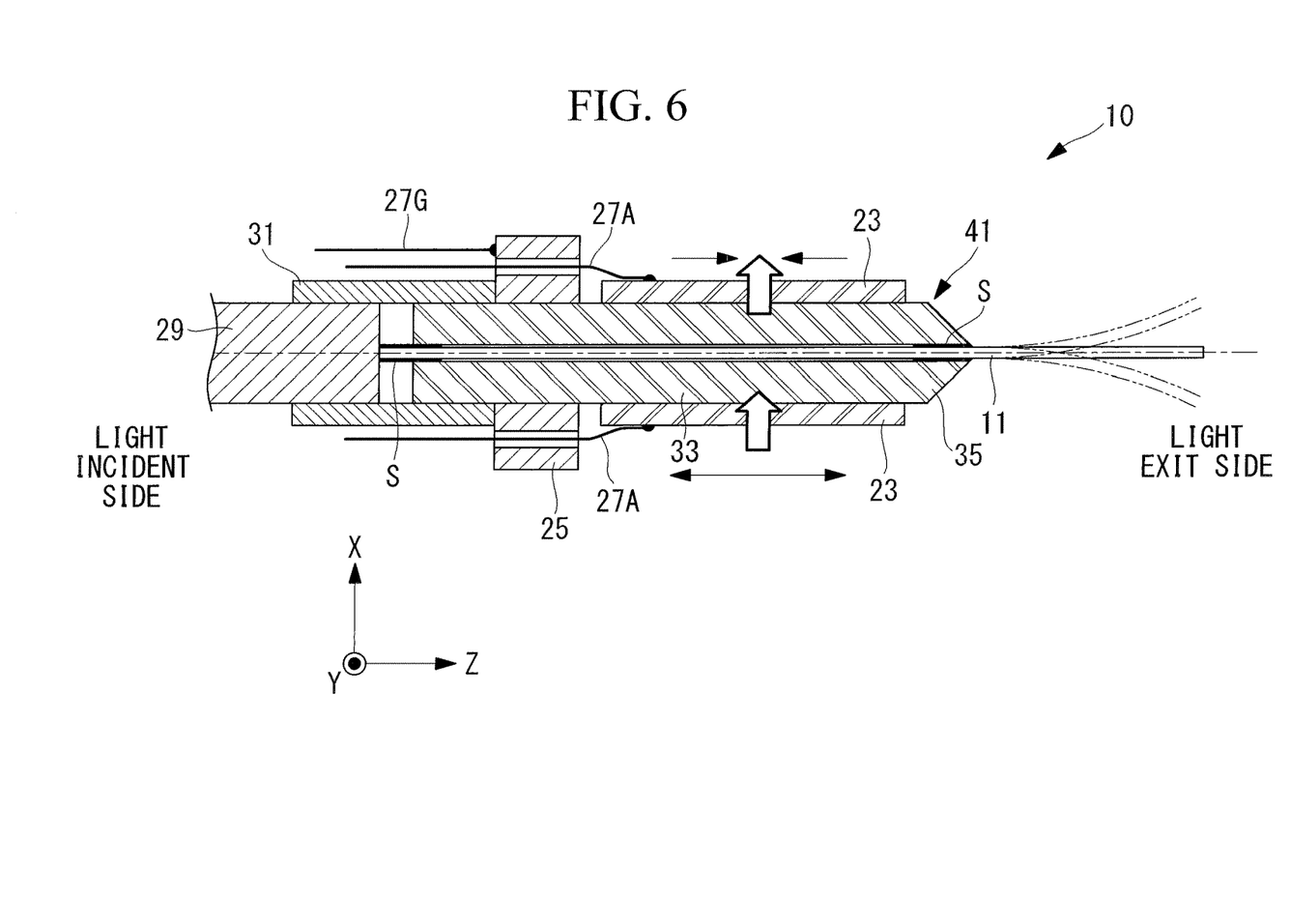
FIG. 6 is a configuration diagram of an optical-fiber scanner according to a first modification of the embodiment of the present invention, taken along the radial direction of an illumination optical fiber.
Figure 7A:
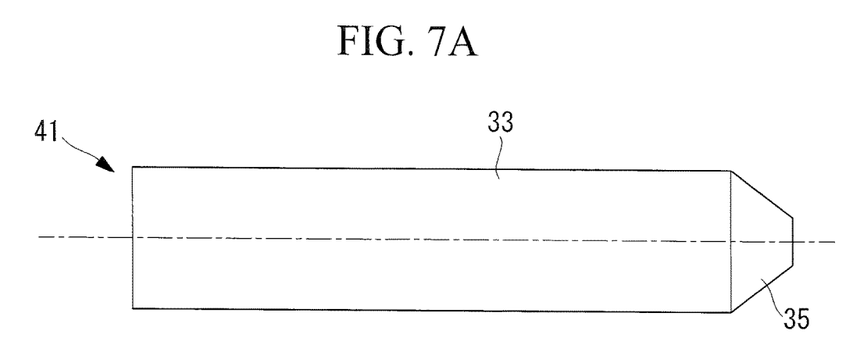
FIG. 7A is a side view of a columnar portion of a vibration-transmitting body in FIG. 6.
Figure 7B:
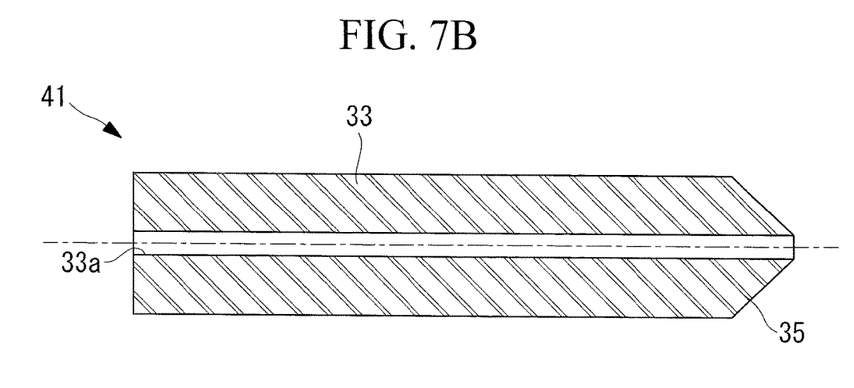
FIG. 7B is a cross-sectional view of the columnar portion of the vibration-transmitting body in FIG. 6, taken along the center axis.
Figure 7C:
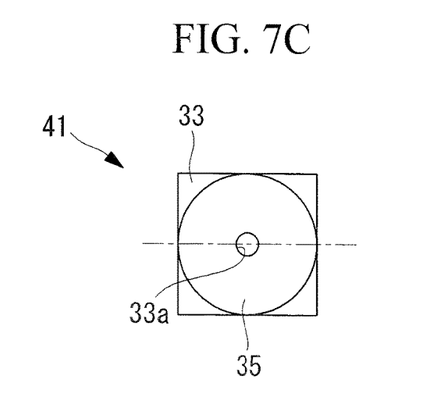
FIG. 7C is a plan view of the columnar portion of the vibration-transmitting body in FIG. 6, viewed in the direction along the center axis.

As shown in FIGS. 5A and 5B, the distal-end portion 35 is formed of a cylindrical attaching portion 35a that is attached to the opening 33b of the columnar portion 33 in a fitted state, and a protrusion 35b that protrudes in the longitudinal direction of the columnar portion 33 in a state in which the attaching portion 35a is attached to the columnar portion 33. The protrusion 35b has a rotator shape that spreads out radially outward from the attaching portion 35a and in which the cross-sectional area thereof in the radial direction gradually decreases so as to form a conical shape away from the attaching portion 35a.

In addition, the distal-end portion 35 has a fitting hole 35c through which the illumination optical fiber 11 is fitted by passing through the attaching portion 35a and the protrusion 35b. As shown in FIG. 2, the fitted illumination optical fiber 11 is attached to the fitting hole 35c by means of the epoxy-based adhesive S applied to the outer circumferential surface of the illumination optical fiber 11.

As shown in FIGS. 2 and 3, the securing portion 25 is formed of a metal material, such as stainless steel or the like, and is formed in a ring shape. An outer circumferential surface of the securing portion 25 is attached to an inner wall of the outer tube 15 by using the epoxy-based adhesive. In addition, the securing portion 25 has a fitting hole 25a in which the columnar portion 33 of the vibration-transmitting body 21 is fitted, and the vibration-transmitting body 21 is firmly secured thereto by filling a conductive epoxy-based adhesive in portions in which gaps are formed when the vibration-transmitting body 21 is fitted to the fitting hole 25a.

The securing portion 25 is configured so that the vibration-transmitting body 21 is fitted thereto, by means of the fitting hole 25a, at a position that is farther on the basal-end side away from the piezoelectric elements 23, thus supporting the illumination optical fiber 11 in a cantilever-like manner. By doing so, the securing portion 25 is configured so as to suppress radial-direction vibrations generated at this position of the illumination optical fiber 11. In addition, even if the vibrations escape from the piezoelectric elements 23 toward the basal end of the illumination optical fiber 11, these vibrations are prevented from returning by undergoing changes in shapes thereof due to the influences of some factors. Therefore, it is possible to prevent, by means of the securing portion 25, the vibration shapes of the piezoelectric elements 23 and vibrations in the illumination optical fiber 11 from being destabilized.

In addition, the securing portion 25 is electrically joined to electrodes on the back surfaces of the four piezoelectric elements 23 via the vibration-transmitting body 21, and is configured so as to serve as a common GND when driving the piezoelectric elements 23. In addition, the securing portion 25 has four through-holes 25b through which the leads 27A and 27B pass. It is desirable that the through-holes 25b be individually formed so as to be parallel to the center axis of the securing portion 25. By doing so, positioning of the leads 25A and 25B with respect to the piezoelectric elements 23 is facilitated, and thus, it is possible to connect the piezoelectric elements 23 without unnecessarily increasing the lengths of the leads 25A and 25B.

As shown in FIG. 2, the jacket 29 covers the illumination optical fiber 11, such that a gap is formed with respect to the vibration-transmitting body 21. The dimensions of the external shape of the jacket 29 are nearly the same as the dimensions of the external shape of the columnar portion 33 of the vibration-transmitting body 21.

The buckling-prevention pipe 31 has a tubular shape and is disposed adjacent to the securing portion 25 along the longitudinal direction of the illumination optical fiber 11. The rear-end portion of the vibration-transmitting body 21, which protrudes toward the basal end of the illumination optical fiber 11 from the securing portion 25, and the distal-end portion of the jacket 29 are fitted together by means of the buckling-prevention pipe 31, and joined surfaces are secured by using an adhesive. By using the jacket 29 and the buckling-prevention pipe 31, it is possible to prevent buckling of the portion of the illumination optical fiber 11 farther on the basal-end side than the vibration-transmitting body 21.

The piezoelectric elements 23 are formed of a piezoelectric ceramic material, for example, lead zirconate titanate (PZT) or the like, and are formed in a long, thin plate-like shape. In addition, the piezoelectric elements 23 are subjected to positive-electrode treatment in front surfaces thereof, are subjected to negative-electrode treatment in back surfaces thereof, and are polarized in a direction from the positive pole to the negative pole, that is, in the plate-thickness direction.

As shown in FIG. 2, at the individual side surfaces of the columnar portion 33 of the vibration-transmitting body 21, the four piezoelectric elements 23 are individually disposed at the same positions in the longitudinal direction of the illumination optical fiber 11. It is desirable that the gaps between the piezoelectric elements 23 and the securing portion 25 be large enough not to hinder expansion/contraction in at least a direction that intersects the polarization directions of the piezoelectric elements 23. By doing so, the securing portion 25 does not hinder the expansion/contraction of the illumination optical fiber 11 in the longitudinal direction caused by the piezoelectric elements 23.

In addition, as shown in FIG. 3 with arrows that indicate the directions of polarization, the respective pairs of piezoelectric elements 23 that face each other in the radial direction of the illumination optical fiber 11 are disposed so that the polarization directions thereof are oriented in the same directions. In addition, by using the conductive epoxy-based adhesive, the leads 27A that form the A phase are joined with the electrode surfaces of the first pair of piezoelectric elements 23, and the leads 27B that form the B phase are joined with the electrode surfaces of the second pair of the piezoelectric elements 23.

The piezoelectric elements 23 are configured so that vibrations (lateral effects) that cause expansion/contraction in directions orthogonal to the polarization directions thereof are generated when alternating voltages are applied thereto in the polarization directions by the leads 27A and 27B. In addition, when one of the piezoelectric elements 23 in a pair contracts, the other piezoelectric element 23 expands. By doing so, the respective pairs of piezoelectric elements 23 transmit these vibrations to the illumination optical fiber 11 via the vibration-transmitting body 21, and thus, the distal end of the illumination optical fiber 11 can be vibrated in directions that intersect the longitudinal direction.

As shown in FIG. 2, one end of the lead 27G is joined to the securing portion 25 by using a conductive epoxy-based adhesive. The leads 27A and 27B are connected to the piezoelectric elements 23 after passing through the through-holes 25b of the securing portion 25, and are secured to the through-holes 25b by using the epoxy-based adhesive.

As shown in FIG. 1, the detection optical fibers 19 are formed of long, thin glass materials, and are disposed at the outer circumferential surface of the outer tube 15 along the longitudinal direction. The detection optical fibers 19 are disposed in the circumferential direction of the outer tube 15 with spaces between each other. In addition, one ends of the detection optical fibers 19 are disposed at the distal end of the outer tube 15, and the other ends thereof are connected to the photodetector 5.

In addition to controlling the illumination apparatus 3 and the photodetector 5, the controller 7 is configured so that image information can be generated by associating return-light intensity signals detected by the photodetector 5 and information about positions scanned by the optical-fiber scanner 10 by using the illumination light (scanning-position information).

The operation of the thus-configured optical-fiber scanner 10, illumination apparatus 3, and endoscope apparatus 100 will now be described.

In order to observe an imaging subject by using the optical-fiber scanner 10, the illumination apparatus 3, and the endoscope apparatus 100 according to this embodiment, first, the distal end of the outer tube 15 is placed so as to face the imaging subject, and the illumination light is generated by the light source 1. The illumination light emitted from the light source 1 is guided by the illumination optical fiber 11 and is emitted from the distal end thereof, and the focusing lens 13 radiates the illumination light onto the imaging subject.

When return light, such as reflected light, fluorescence, or the like, is generated at the imaging subject due to irradiation with the illumination light, this return light is guided by the detection optical fibers 19 and is detected by the photodetector 5. Then, the controller 7 associates the return-light intensity signals output from the photodetector 5 with the scanning-position information of the optical-fiber scanner 10, thus converting the signals to image information. By doing so, an image of the imaging subject irradiated with the illumination light can be generated.

Next, scanning of the illumination light by the optical-fiber scanner 10 will be described.

In order to scan the illumination light by using the optical-fiber scanner 10, first, a flexural resonance frequency of the illumination optical fiber 11, at which a node occurs in the vicinity of the center of the securing portion 25 in the axial direction and an antinode occurs in the distal-end portion of the illumination optical fiber 11, is excited.

When an alternating voltage corresponding to the flexural resonance frequency is applied to the first pair of piezoelectric elements 23 (hereinafter, referred to as A-phase piezoelectric elements 23), vibrations are generated in these A-phase piezoelectric elements 23. Then, the vibrations generated in the A-phase piezoelectric elements 23 are transmitted to the illumination optical fiber 11 via the vibration-transmitting body 21, and thus, the distal-end portion of the illumination optical fiber 11 is vibrated in one direction that intersects the longitudinal direction (for example, the X-axis (A phase) direction in FIGS. 1 to 3).

Similarly, when an alternating voltage corresponding to the flexural resonance frequency is applied to the second pair of piezoelectric elements 23 (hereinafter, referred to as B-phase piezoelectric elements 23), vibrations are generated in these B-phase piezoelectric elements 23. Then, the vibrations generated in the B-phase piezoelectric elements 23 are transmitted to the illumination optical fiber 11 via the vibration-transmitting body 21, and thus, the distal-end portion of the illumination optical fiber 11 is vibrated in one direction that is orthogonal to the X-axis direction (for example, the Y-axis (B phase) direction in FIGS. 1 to 3).

By simultaneously generating the X-axis-direction vibrations due to the A-phase piezoelectric elements 23 and the Y-axis direction vibrations due to the B-phase piezoelectric elements 23, and by shifting, by $\pi/2$, the phases of the alternating signals to be applied to the A-phase piezoelectric elements 23 and the B-phase piezoelectric elements 23, the vibrations in the distal-end portion of the illumination optical fiber 11 follow a circular track. When the magnitude of the alternating voltages to be applied to the A-phase piezoelectric elements 23 and the B-phase piezoelectric elements 23 is gradually increased and decreased (causing voltage modulations) in this state, the distal end of the illumination optical fiber 11 is vibrated in a spiraling manner. By doing so, the illumination light emitted from the distal end of the illumination optical fiber 11 can be scanned on the imaging subject in a spiraling manner.

In this case, with the optical-fiber scanner 10 according to this embodiment, because the distal-end portion 35 that supports the illumination optical fiber 11 in the vibration-transmitting body 21 in the fitted state has the rotator shape in which the cross-sectional area thereof in the radial direction gradually decreases from the columnar portion 33 toward the distal end of the illumination optical fiber 11, changes in the cross-sectional area are gradually decreased from the portion in which the illumination optical fiber 11 is fitted to the distal-end portion 35 to the portion in which the distal end of the illumination optical fiber 11 is exposed.

By doing so, it is possible to prevent stress generated by the vibrations transmitted from the vibration-transmitting body 21 to the illumination optical fiber 11 from concentrating at one point in the vicinity of the distal end of the illumination optical fiber 11, and thus, it is possible to prevent breakage of the illumination optical fiber 11 due to abrupt changes in stress. Therefore, it is possible to smoothly transmit the vibrations generated in the piezoelectric elements 23 to the illumination optical fiber 11 by means of the vibration-transmitting body 21, and thus, it is possible to stably vibrate the illumination optical fiber 11.

In addition, by forming the columnar portion 33 and the distal-end portion 35 of the vibration-transmitting body 21 as separate pieces, it is possible, for example, to form the columnar portion 33 and the distal-end portion 35 by using different materials, and to easily make the size of the through-hole 33a of the columnar portion 33 and that of the fitting hole 35c of the distal-end portion 35 different.

In addition, with the illumination apparatus 3 according to this embodiment, by using such an optical-fiber scanner 10, it is possible to precisely illuminate a desired position in the imaging subject. Furthermore, with the endoscope apparatus 100 according to this embodiment, it is possible to realize accurate observation on the basis of image information of a desired observation area in the imaging subject, which is obtained on the basis of return-light intensity signals detected by the photodetector 5.

It is possible to modify this embodiment as described below.

In this embodiment, the vibration-transmitting body 21 in which the columnar portion 33 and the distal-end portion 35 are formed as separate pieces has been described as an example of the vibration-transmitting body. Alternatively, it is permissible to employ, as a first modification, a vibration-transmitting body 41 in which the columnar portion 33 and the distal-end portion 35 are molded as a single piece, as shown in FIGS. 6, 7A, 7B, and 7C.

By doing so, looseness or the like due to variability in processing precision between the distal-end portion 35 and the columnar portion 33 does not occur in the vibration-transmitting body 41. Therefore, it is possible to more smoothly transmit the vibrations in the piezoelectric elements 23 to the illumination optical fiber 11 via the vibration-transmitting body 41.

Figure 8:
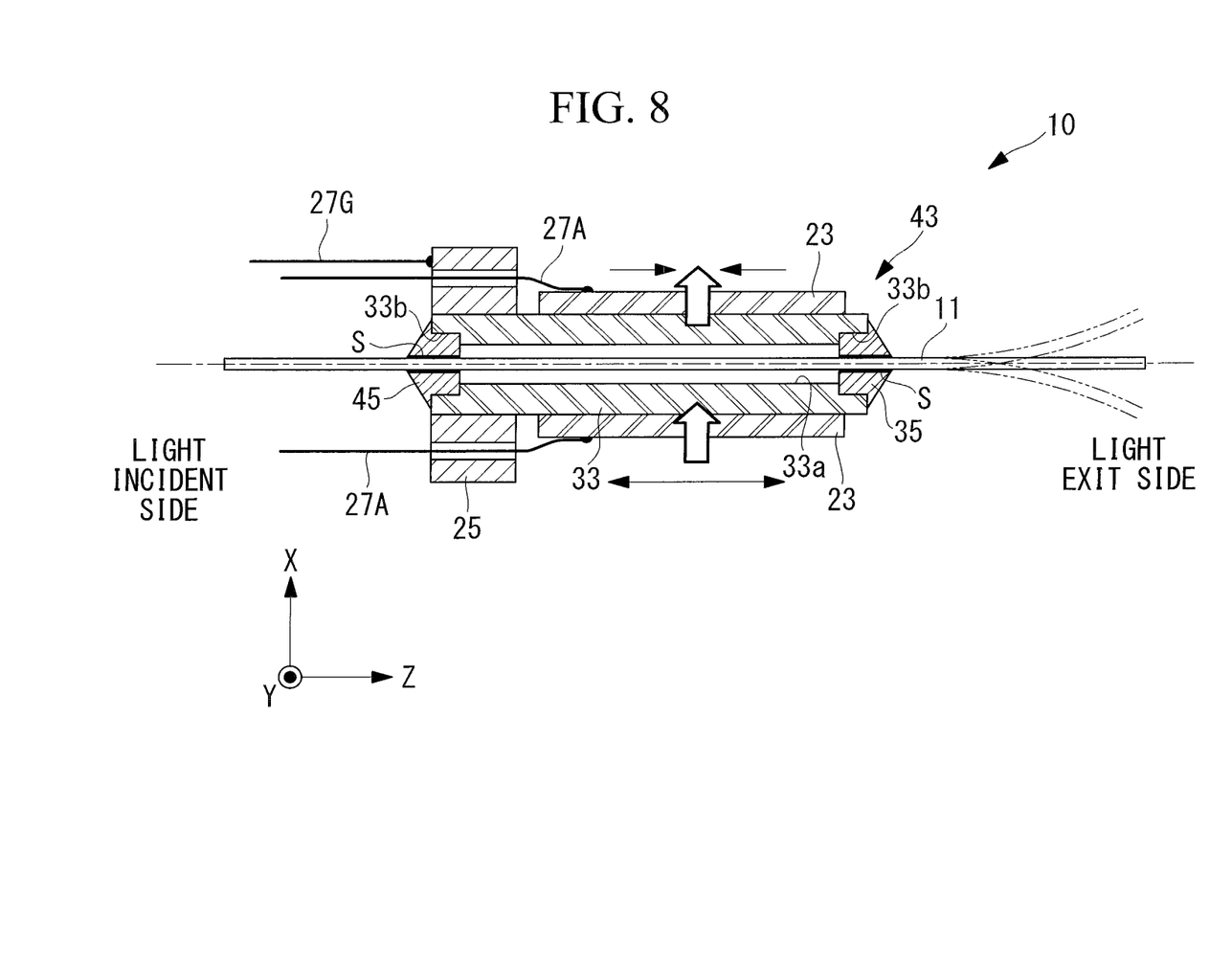
FIG. 8 is a configuration diagram of an optical-fiber scanner according to a second modification of the embodiment of the present invention, taken along the radial direction of an illumination optical fiber.

As a second modification, it is permissible to employ, as the vibration-transmitting body, for example, a vibration-transmitting body 43 that includes a rear-end portion 45 having the same shape as the distal-end portion 35, as shown in FIG. 8. In this case, the columnar portion 33 may have, at both ends in the longitudinal direction, the openings 33b in which the shapes thereof include a level difference where the opening areas of the through-holes 33a increase radially outward, and the distal-end portion 35 and the rear-end portion 45 may be held in the fitted state by means of the individual openings 33b.

With this modification, it is possible to utilize the vibration-transmitting body 43 when disposed with the distal-end portion 35 pointing toward the distal end of the illumination optical fiber 11, as well as when disposed with the rear-end portion 45 pointing toward the distal end of the illumination optical fiber 11. In addition, because the vibration-transmitting body 43 is a minute component, eliminating the need to consider the orientation of the vibration-transmitting body 43 during manufacturing decreases the complexity of manufacturing. In addition, by forming the columnar portion 33, the distal-end portion 35, and the rear-end portion 45 as separate pieces, it is possible to form these components by using different materials, and to easily make the size of the through-hole 33a of the columnar portion 33 and those of the fitting holes 35c of the distal-end portion 35 and the rear-end portion 45 different.

Figure 9:
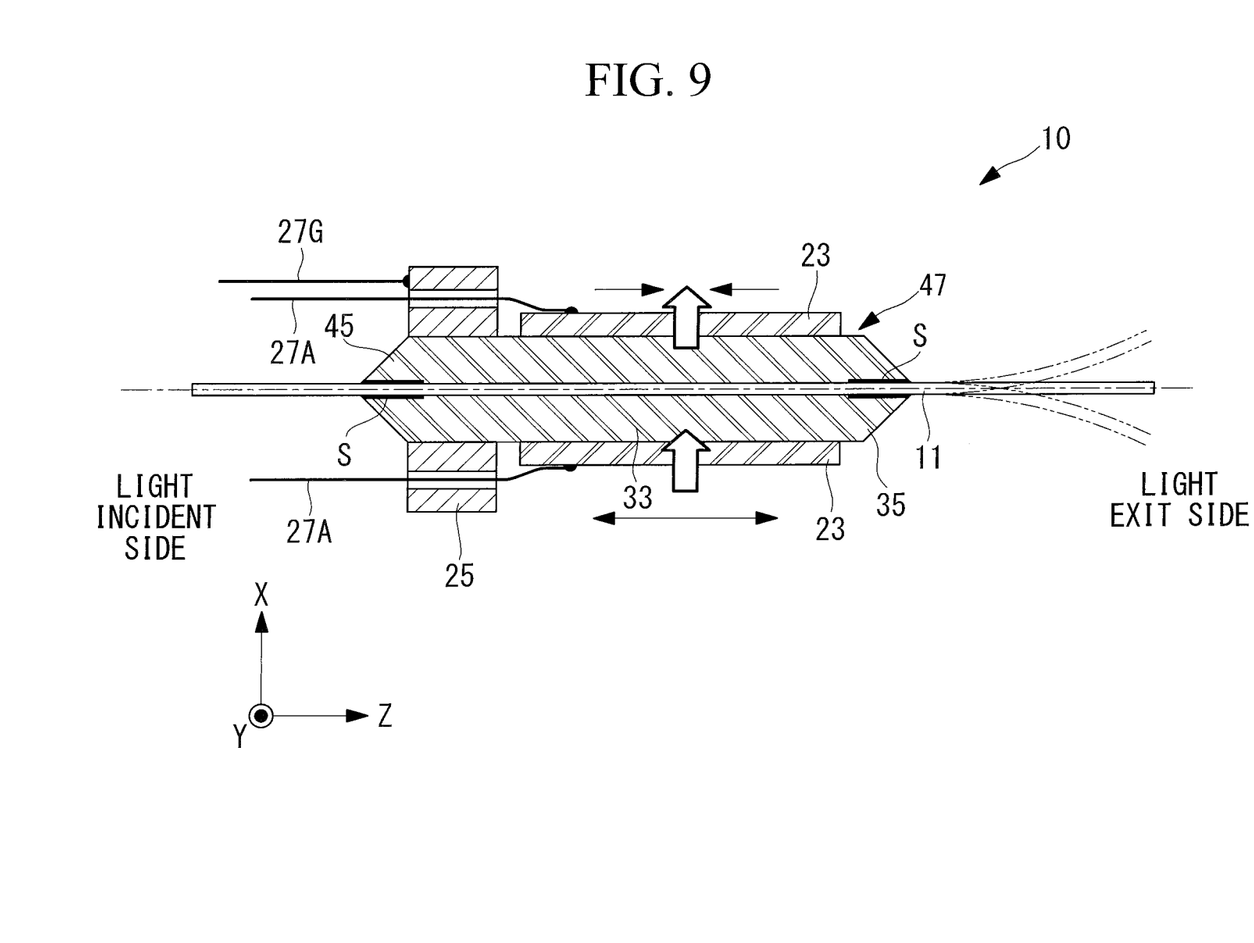
FIG. 9 is a configuration diagram of an optical-fiber scanner according to a third modification of the embodiment of the present invention, taken along the radial direction of an illumination optical fiber.

In this modification, the vibration-transmitting body 43 in which the columnar portion 33, the distal-end portion 35, and the rear-end portion 45 are formed as separate pieces has been described as an example. Alternatively, it is permissible to employ, as a third modification, a vibration-transmitting body 47 in which the columnar portion 33, the distal-end portion 35, and the rear-end portion 45 are molded as a single piece, as shown in FIG. 9.

By doing so, looseness or the like due to variability in processing precision between the columnar portion 33 and both the distal-end portion 35 and the rear-end portion 45 does not occur in the vibration-transmitting body 47. Therefore, it is possible to more smoothly transmit the vibrations in the piezoelectric elements 23 to the illumination optical fiber 11 via the vibration-transmitting body 47.

As has been described above, although the embodiment of the present invention has been described in detail with reference to the drawings, specific configurations are not limited to this embodiment, and design alterations or the like that do not depart from the scope of the present invention are also encompassed. For example, the present invention is not limited to the applications in the embodiment and the modifications thereof, described above; the present invention may be applied to embodiments in which these embodiments and modifications thereof are appropriately combined, and it is not particularly limited.

As a result, the above-described embodiment leads to the following aspects.

A first aspect of the present invention is an optical-fiber scanner including: an optical fiber that guides light to emit the light from a distal end thereof; a vibration-transmitting body that is fitted to a portion farther on a basal end side of the distal end of the optical fiber and that can transmit vibrations to the optical fiber; a plurality of piezoelectric elements that are secured to the vibration-transmitting body, that are polarized in radial directions of the optical fiber, and that cause the optical fiber to vibrate via the vibration-transmitting body when alternating voltages are applied thereto in the polarization directions; and a support portion that has a fitting hole to which the vibration-transmitting body is fitted at a position that is farther on a basal-end side away from the piezoelectric elements, and that can support the optical fiber in a cantilever-like manner via the vibration-transmitting body fitted to the fitting hole, wherein the vibration-transmitting body has a hollow columnar portion that is formed of an elastic material, to which the plurality of piezoelectric elements are attached at side surfaces thereof, and that has a through-hole through which the optical fiber can be inserted, and a distal-end portion that is disposed at a distal end of the columnar portion, that supports the optical fiber in a fitted state, and that has a rotator shape in which a cross-sectional area thereof in a radial direction gradually decreases toward a distal end of the optical fiber.

With this aspect, when alternating voltages are applied to the piezoelectric elements in the polarization directions thereof, the piezoelectric elements expand and contract in directions that are orthogonal to the polarization directions, that is, the longitudinal direction of the optical fiber, thus generating vibrations, and the vibrations in the piezoelectric elements are transmitted to the optical fiber via the vibration-transmitting body. In addition, by supporting the optical fiber in a cantilever-like manner by means of the support portion via the vibration-transmitting body, the vibrations generated in the piezoelectric elements that escape toward the basal end of the optical fiber are suppressed. By doing so, it is possible to stably vibrate the distal end of the optical fiber, and thus, it is possible to precisely scan the light emitted from the distal end of the optical fiber in accordance with the vibrations of the optical fiber.

In this case, because the distal-end portion that supports the optical fiber in the vibration-transmitting body in the fitted state has the rotator shape in which the cross-sectional area thereof in the radial direction gradually decreases from the columnar portion toward the distal end of the optical fiber, changes in the cross-sectional area are gradually decreased from the portion in which the optical fiber is fitted to the distal-end portion to the portion in which the distal end of the optical fiber is exposed. By doing so, it is possible to prevent stress generated by the vibrations transmitted from the vibration-transmitting body to the optical fiber from concentrating at one point in the vicinity of the distal end of the optical fiber, and thus, it is possible to prevent breakage of the optical fiber due to abrupt changes in stress. Therefore, it is possible to smoothly transmit the vibrations generated in the piezoelectric elements to the optical fiber by means of the vibration-transmitting body, and thus, it is possible to stably vibrate the optical fiber.

In the above-described aspect, the distal-end portion may be formed in the columnar portion as a separate piece.

By employing such a configuration, it is possible to form the distal-end portion and the columnar portion constituting the vibration-transmitting body by using different materials, and to make the sizes of the through-holes into which the optical fiber is inserted different between the distal-end portion and the columnar portion.

In the above-described aspect the distal-end portion and the columnar portion may be molded as a single piece.

By employing such a configuration, looseness or the like due to variability in processing precision between the distal-end portion and the columnar portion does not occur in the vibration-transmitting body. Therefore, it is possible to more smoothly transmit the vibrations in the piezoelectric elements to the optical fiber.

A second aspect of the present invention is an illumination apparatus including: any one of the above-described optical-fiber scanners; a light source that generates the light to be guided by the optical fiber; a focusing lens that focuses the light emitted from the optical fiber; and an outer tube that holds the focusing lens and the optical-fiber scanner.

With this aspect, it is possible to precisely illuminate a desired position in the imaging subject by using the optical-fiber scanner that is capable of causing stable bending vibrations in the optical fiber.

A third aspect of the present invention is an observation apparatus including: the above-described illumination apparatus; and a light-detecting portion that detects return light returning from an imaging subject and generated by radiating the light onto the imaging subject with the illumination apparatus.

With this aspect, the illumination apparatus precisely scans the light at a desired position of the imaging subject, and thus, the return light returning from the imaging subject is detected by the light-detecting portion. Therefore, it is possible to realize accurate observation on the basis of image information of a desired observation area in the imaging subject, which is obtained on the basis of return-light intensity signals detected by the light-detecting portion.

The present invention affords an advantage in that it is possible to cause stable bending vibrations in an optical fiber.

REFERENCE SIGNS LIST 1 light source
3 illumination apparatus
5 photodetector (light-detecting portion)
10 optical-fiber scanner
11 illumination optical fiber (optical fiber)
13 focusing lens
15 outer tube
21, 41, 43, 47 vibration-transmitting body
23 piezoelectric element
25 securing portion (support portion)
25a fitting hole
33 columnar portion 33a through-hole
35 distal-end portion
100 endoscope apparatus (observation apparatus)

The invention claimed is:

1. An endoscope apparatus comprising:
an optical fiber that radiates illumination light, which has entered from a basal end thereof, onto an imaging subject from a distal end thereof;
a support that secures the optical fiber;
a piezoelectric element that is disposed farther on the distal-end side of the optical fiber than the support is, and that causes the optical fiber to vibrate in accordance with an alternating signal applied thereto;
a photodetector that detects return light coming from the imaging subject that has been irradiated with the illumination light;
a jacket that is disposed farther on the basal-end side of the optical fiber than the support is and that covers the optical fiber; and
a buckling-prevention pipe that is disposed along a longitudinal direction of the optical fiber, and that is secured to the support and the jacket.

2. An endoscope apparatus according to claim 1, wherein the buckling-prevention pipe has a tubular shape.

3. An endoscope apparatus according to claim 1, wherein the support is provided with a vibration-transmitting body that is formed in a columnar shape having a through-hole and to which the piezoelectric element is attached,
and a support portion that has a fitting hole to which the vibration-transmitting body is fitted and that supports the optical fiber via the vibration-transmitting body,
the optical fiber is disposed in the through-hole,
the vibration-transmitting body is secured in the fitting hole, and
the buckling-prevention pipe is secured at a basal-end portion of the vibration-transmitting body and a distal-end portion of the jacket.

4. An endoscope apparatus according to claim 3, wherein the buckling-prevention pipe is disposed adjacent to the support, is fitted to the basal-end portion of the vibration-transmitting body and the distal-end portion of the jacket, and is secured, at fitted surfaces thereof, to the vibration-transmitting body and the jacket by using an adhesive.

5. An endoscope apparatus according to claim 4, wherein dimensions of an external shape of the jacket are the same as dimensions of an external shape of the vibration-transmitting body.

* * * * *